United States Patent [19]

Martin et al.

[11] Patent Number: 5,698,532

[45] Date of Patent: Dec. 16, 1997

[54] PYRIMIDINE NUCLEOSIDES AND METHODS FOR TREATING VIRAL INFECTIONS WITH SAME

[75] Inventors: Joseph Armstrong Martin, Harpenden; Gareth John Thomas, Welwyn, both of England

[73] Assignee: Hoffmann-La Roche Inc., Nutley, N.J.

[21] Appl. No.: 677,704

[22] Filed: Jul. 10, 1996

[30] Foreign Application Priority Data

Jul. 13, 1995 [GB] United Kingdom ............ 9514268

[51] Int. Cl.$^6$ .................................................. A61K 31/70
[52] U.S. Cl. ............................. 514/49; 514/50; 514/51; 514/931; 514/933; 536/28.53; 536/28.54
[58] Field of Search ............................. 514/49, 50, 51, 514/931, 933; 536/28.53, 28.54

[56] References Cited

U.S. PATENT DOCUMENTS

| 4,851,519 | 7/1989 | Lambert et al. . |
| 4,886,785 | 12/1989 | Lambert et al. . |
| 4,956,346 | 9/1990 | Lambert et al. . |
| 5,010,060 | 4/1991 | Lambert et al. . |

FOREIGN PATENT DOCUMENTS 257 387  8/1996  European Pat. Off. .

*Primary Examiner*—James O. Wilson
*Attorney, Agent, or Firm*—George W. Johnston; Patricia S. Rocha Tramaloni

[57] ABSTRACT

This invention is directed to the novel pyrimidine derivative 1-[5-[2(S)-(2,4-dichloro-5-methoxyphenoxy) propionamido]-2,5-dideoxy-2-fluoro-β-D-arabinofuranosly]-5-ethyluracil and its use as an antiviral agent, as well as to intermediates useful in the synthesis of this compound.

3 Claims, No Drawings

PYRIMIDINE NUCLEOSIDES AND METHODS FOR TREATING VIRAL INFECTIONS WITH SAME

SUMMARY OF THE INVENTION

The present invention is concerned with a pyrimidine nucleoside derivative, a process for its manufacture and novel intermediates in this process. The invention is further concerned with pharmaceutical preparations containing this pyrimidine derivative.

DETAILED DESCRIPTION OF THE INVENTION

The pyrimidine nucleoside derivative provided by the present invention is 1-[5-[2(S)-(2,4-dichloro-5-methoxyphenoxy) propionamido]-2,5-dideoxy-2-fluoro-β-D-arabino -furanosyl]-5-ethyluracil of the formula

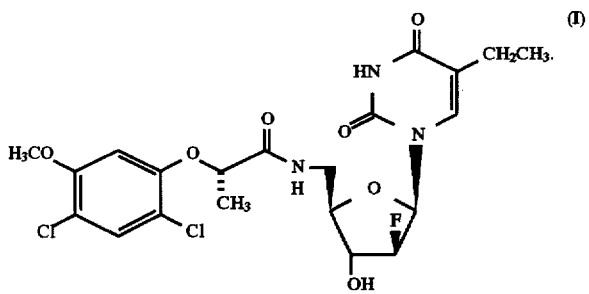

The compound of formula I has valuable pharmacological properties. In particular, it inhibits viral thymidine kinase and is accordingly useful in the treatment or prophylaxis of viral infections, especially those caused by herpes simplex virus (HSV).

The compound of the present invention belongs to a group of compounds generally disclosed in European patent No. 257 378. As is demonstrated herein, however, the compound of formula I has significant and unexpected advantages over closely related compounds within EP 257 378. Specifically, the compounds of formula I has higher activity/enhanced bioavailability following oral administration than the compounds of EP 257 378 with which it was compared (see below).

According to the process provided by the present invention, the compound of formula I is manufactured by reacting 1-(5-amino-2,5-dideoxy-2-fluoro-β-D-arabinofuranosyl)-5-ethyluracil of the formula

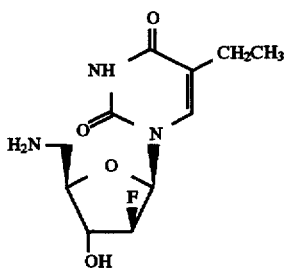

with (S)-2-(2,4-dichloro-5-methoxyphenoxy)-propionic acid of the formula

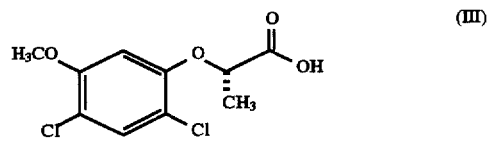

or a reactive derivative thereof.

In a preferred procedure the propionic acid of formula III is used in the form of a conventional reactive derivative, e.g. an acid anhydride or especially an acid halide, preferably the acid chloride, which is conveniently prepared by reacting the acid with oxalyl chloride in a known manner. Alternatively, the acid itself may be used in the presence of dicyclohexylcarbodiimide or a similar activating reagent.

The reaction can be carried out in a manner known to those skilled in the art. Suitably, it is carried out in the presence of an inert organic solvent, e.g. an open-chain or cyclic ether such as diethyl ether or tetrahydrofuran or an aromatic hydrocarbon such as benzene, and in the presence of an inorganic base, e.g. an alkali metal hydroxide such as sodium hydroxide or potassium hydroxide, or an organic base such as pyridine. Further, the reaction is conveniently carried out at about 0° C. to about room temperature.

The amine starting material of formula II is a known compound.

The acid starting material of formula III is also a known compound which can be prepared, for example, as illustrated in the following Reaction Scheme:

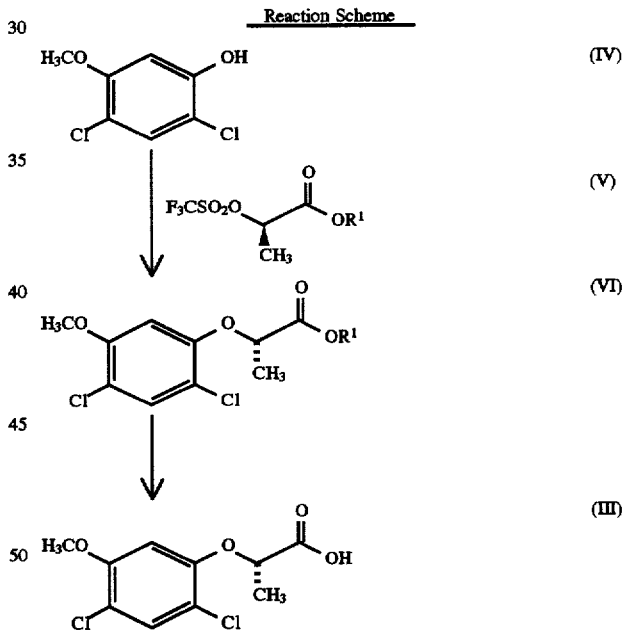

wherein $R^1$ represents $C_{1-4}$-alkyl.

The above described reactive steps can be carried out in a manner known to those skilled in the art. Thus, in the first step, 2,4-dichloro-5-methoxyphenol of formula IV is reacted with an alkyl (R)-2-trifluoromethanesulphonyloxypropionate of formula V. This reaction, in which the methyl ester of formula V is preferably used, is conveniently carried out in an inert organic solvent, e.g. acetonitrile, in the presence of a base, e.g. an alkali metal carbonate such as sodium or potassium carbonate, and at an elevated temperature. The conversion of the resulting alkyl (S)-2-(2,4-dichloro-5-methoxyphenoxy)-propionate of formula VI, which is a novel compound and as such forms an object of the present invention, into (S)-2-(2,4-dichloro-5- methoxyphenoxy)-propionic acid of formula III is carried out in a manner known in the art, for example by treatment with a solution of an alkali metal hydroxide such as sodium or potassium hydroxide in an aqueous alkanol, e.g. aqueous ethanol, at room temperature.

The compounds of formula IV and V used as starting materials in the foregoing Reaction Scheme are known compounds.

The compound of formula I is useful as an antiviral agent. Moreover, as is shown below in Table 1, the compound of formula I has unexpectedly higher activity coupled with enhanced bioavailability following oral administration in comparison to structurally related compounds disclosed in EP 257 378.

ACTIVITY ASSAY

The activity, of the compound of formula I can be demonstrated on the basis of the following test procedure for the inhibition of HSV-2 thymidine kinase, a standard assay used in the pharmaceutical industry to assess viral inhibition (Honess, et al., J. Gen. Virol. 58:237–249 (1982)).

In this test procedure, the assay mixture contains 50 mmol Tris HCl, pH 8, 5 mmol magnesium chloride, 5 mmol ATP, 0.3 µmol $^3$H-thymidine (50 Ci/mmol), suitably diluted enzyme preparation and various concentrations of test compounds in a total volume of 100 µl. Assays are incubated at 37° C. for 30 minutes and the reaction is terminated by immersion in a boiling water bath for 2 minutes. 85 µl aliquots from each assay are then dried on to DEAE-cellulose paper discs and the unphosphorylated $^3$H-thymidine is removed by washing in 4 mmol ammonium formate. The radioactivity remaining bound to the discs is then measured by scintillation spectrophotometry. The degree of inhibition at each concentration of test compound is expressed as a percentage of the control reaction (100%) after subtracting a measured blank value which represents the amount of radioactivity bound to the disc from a reaction containing heat-inactivated enzymes. The $IC_{50}$ value, namely the concentration of test compound which inhibits enzyme activity by 50%, is then calculated.

| Compound | Activity against HSV-2 TK $IC_{50}$ (nmol) | Oral bioavailability (rat) |
|---|---|---|
| Compound (I) | 0.18 | 26% |
| Compound A | 3.7 | 2.84%[1] |
| Compound B | 4.0 | 14.4%[1] |
| | | 12.9%[2] |

Compound A: 1-[5-[2(RS)-(2,4-Dichlorophenoxy)propionamido]-2,5-dideoxy-β-D-arabinofuranosyl]-5-ethyluracil.
Compound B: 1-[5-[2(RS)-(2,4-Dichlorophenoxy)propionamido]-2,5-dideoxy-2-fluoro-β-D-arabinofuranosyl]-5-ethyluracil.
[1]Diastereoisomer a
[2]Diastereoisomer b Oral bioavailability of compound A, diastereoisomer b, was too low to calculate.

The compound of formula I can be used as a medicament, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compound of formula I can be processed with pharmaceutically inert, organic or inorganic carriers for the production of pharmaceutical preparations. Lactose, corn starch or derivatives thereof, talc, stearic acid or its salts and the like can be used, for example, as carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, saccharose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing the compound of formula I and a therapeutically inert excipient are also an object of the present invention, as is a process for the production of such medicaments which comprises bringing the compound of formula I and, if desired, one or more other therapeutically valuable substances into a galenical administration form together with a compatible pharmaceutical carrier.

As mentioned earlier, the compound of formula I can be used in accordance with the invention as a therapeutically active substance, especially as an antiviral agent. The dosage can vary within wide limits and will, of course, be fitted to the individual requirements in each particular case. In general, in the case of administration to adults (weighing approximately 75 kg) a daily dosage of about 1 mg to 1000 mg, preferably about 5 mg to 500 mg or about 50 mg to 250 mg, should be appropriate. The daily dosage may be administered as a single dose or in divided doses.

Finally, the use of the compound of formula I for the production of medicaments, especially of antiviral medicaments, is also an object of the invention.

The following Examples are intended to illustrate the present invention in more detail, but are not intended to limit its scope in any manner.

EXAMPLE 1

Preparation of 1-[5-[2(S)-(2,4-dichloro-5-methoxyphenoxy)propionamido]-2,5-dideoxy-2-fluoro-β-D-arabinofuranosyl]-5-ethyluracil 24.2 g (0.091 mol) of (S)-2-(2,4-dichloro-5-methoxyphenoxy)-propionic acid were suspended in a mixture of 150 ml of toluene and 0.5 ml of dimethylformamide and the suspension was stirred under nitrogen. 15.0 ml (0.17 mol) of oxalyl chloride were added, with vigorous evolution of gas occurring. The mixture was stirred for 1 hour to give a homogeneous solution. The solvents were removed by evaporation, the residue was taken up in 100 ml of diethyl ether and the solution was added to a solution of 24.6 g (0.090 mol) of 1-(5-amino-2,5-dideoxy-2-fluoro-β-D-arabinofuranosyl)-5-ethyluracil in 290 ml of 0.31M sodium hydroxide solution. The heterogeneous mixture was shaken vigorously for 10 minutes to give a white precipitate which was filtered off and washed firstly with water and then with diethyl ether. The crude product was recrystallized from hot methanol to give 33.1 g (69.7%) of 1-[5-[2(S)-(2,4-dichloro-5-methoxyphenoxy)propionamido]-2,5-dideoxy-2-fluoro-β-D-arabinofuranosyl]-5-ethyluracil as a white crystalline solid, m.p. 195°–196° C.

The (S)-2-(2,4-dichloro-5-methoxyphenoxy)-propionic acid used as the starting material was prepared as follows:

A mixture of 29.6 g (0.125 mol) of methyl (R)-2-trifluoromethanesulphonyloxypropionate, 24.16 g (0.125 mol) of 2,4-dichloro-5-methoxyphenol and 17.52 g (0.127 mol) of potassium carbonate in 400 ml of acetonitrile was stirred under nitrogen and heated to 70° C. for 1 hour. The mixture was left to cool to room temperature and filtered. The flitrate was evaporated and the residue was partitioned between 400 ml of ethyl acetate and 400 ml of water. The separated organic phase was dried over anhydrous magnesium sulphate and evaporated to give 34.4 g (98.4%) of methyl (S)-2-(2,4-dichloro-5-methoxyphenoxy)-propionate as a pale yellow oil which crystallized on standing.

125 ml (0.125 mol) of 1M sodium hydroxide solution were added to a solution of 34.9 g (0.125 mol) of methyl (S)-2-(2,4-dichloro-5-methoxyphenoxy)-propionate in 200 ml of ethanol. The solution was stirred at room temperature for 40 minutes and then adjusted to pH 1 with 2M hydrochloric acid. Most of the solvent was evaporated and the residue was partitioned between 400 ml of ethyl acetate and 400 ml of water. The separated organic phase was dried over anhydrous magnesium sulphate and evaporated to give 32.4 g (97.7%) of (S)-2-(2,4-dichloro-5-methoxyphenoxy)-propionic acid as a white solid, m.p. 114°–115° C.

The following Example illustrates a pharmaceutical preparation containing the compound of formula I.

EXAMPLE A

Tablets containing the following ingredients may be produced in a conventional manner:

| Ingredient | Per tablet |
| --- | --- |
| Compound of formula I | 100 mg |
| Lactose | 70 mg |
| Maize starch | 70 mg |
| Polyvinylpyrrolidone | 5 mg |
| Magnesium stearate | 5 mg |
| Tablet weight | 250 mg |

We claim:

1. A compound having the formula

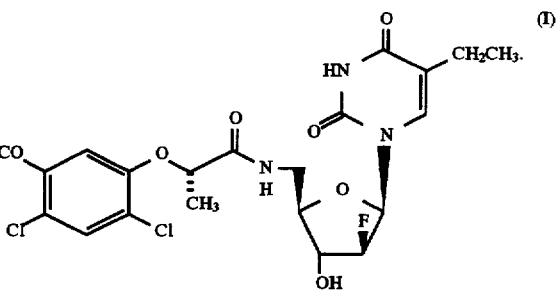

2. A pharmaceutical composition comprising a compound of formula I as set forth in claim 1 and an acceptable carrier.

3. A method for treating a viral infection in a host in need thereof comprising administering to said host an effective antiviral amount of a compound of formula I as set forth in claim 1.

* * * * *